United States Patent [19]

Madsen

[11] 4,313,348

[45] Feb. 2, 1982

[54] METHOD OF STRESS GRADING TIMBER LENGTH

[75] Inventor: Borge S. Madsen, North Vancouver, Canada

[73] Assignee: South African Inventions Development Corp., Pretotia, South Africa

[21] Appl. No.: 143,962

[22] Filed: Apr. 25, 1980

[30] Foreign Application Priority Data

May 2, 1979 [ZA] South Africa ............... 79/2112

[51] Int. Cl.³ .................................. G01N 3/20
[52] U.S. Cl. ........................................ 73/852
[58] Field of Search .............. 73/852, 849, 812; 209/517, 518

[56] References Cited

U.S. PATENT DOCUMENTS 3,143,878  8/1964  Hoyle et al. ................. 73/852
3,194,063  7/1965  McKean ....................... 73/852
3,760,636  9/1973  Serry ........................... 73/852

FOREIGN PATENT DOCUMENTS 1056167  1/1967  United Kingdom .
1145702  3/1969  United Kingdom .
1322953  7/1973  United Kingdom .
1377607  12/1974 United Kingdom .
1466741  3/1977  United Kingdom .

Primary Examiner—Anthony V. Ciarlante
Attorney, Agent, or Firm—Ladas & Parry

[57] ABSTRACT

This invention provides a method of stress grading timber lengths. The minimum stiffness and clear stiffness of the timber lengths are measured and the timber lengths are classified using both the minimum stiffnesses and clear stiffnesses as predictors to predict the load bearing ability of each timber length when loaded as a simple beam.

15 Claims, 1 Drawing Figure

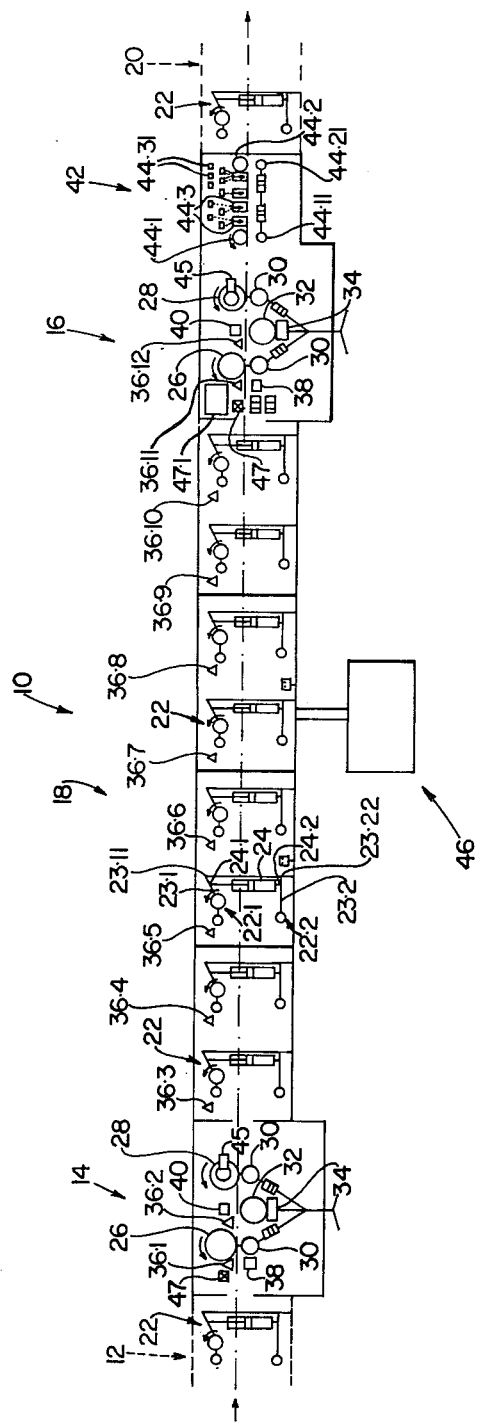

METHOD OF STRESS GRADING TIMBER LENGTH

This invention relates to a method of stress grading a timber length.

By "stress grading" is meant stressing the timber length by applying a load to the length of timber, and relating the load applied to a deflection of the timber caused by the load, thereby to assign the timber to one of two or more, more or less arbitrary, grades, depending on the stiffness of the timber length, i.e. the deflection obtained for a particular load. In this regard the modulus of elasticity of the timber length, which is derived directly from stiffness, can be used equally easily as the criterion for grading.

According to the invention a method of stress-grading a timber length in terms of its load-bearing ability when loaded as a simple beam, comprises
measuring the minimum stiffness of the timber length;
measuring the clear stiffness of the timber length; and
using the independent predictors constituted by said minimum stiffness and said clear stiffness in conjuction to classify the timber length into a particular grade according to its load-bearing ability when loaded as a simple beam.

As mentioned above, the minimum modulus of elasticity of the timber length is frequently used as a measure of stiffness, as these are directly related to each other by well known relationships. Thus after measuring the minimum and clear stiffness, the minimum and clear modulus of elasticity can be obtained therefrom and can be used as the predictors in accordance with the method of the invention. In this regard "clear" stiffness and "clear" modulus of elasticity refer to the average stiffness or average modulus of elasticity of the timber length at a plurality of positions where the length is more or less clear of imperfections and defects such as knots, disease, mechanical damage such as holes, etc.

Measuring the clear and minimum stiffness of the timber length may comprise stressing the timber length at a plurality of positions along its length while it is supported as a beam, each stressing comprising loading the length, in its weak direction, transversely between two spaced supports supporting the length, and the load and the deflection caused by the load being related to determine the stiffness.

Measuring the minimum stiffness of the timber length may comprise stressing the timber length at a plurality of closely spaced positions along its length while the timber length is supported so that each stressing is midway between the supports, determining the stiffness of the timber length at each position where it is stressed, and selecting the minimum value for stiffness so obtained as the minimum stiffness of the timber length.

The closely spaced positions may be spaced apart by spacings which are of the order of the size of the knots anticipated to be encountered in the type or species of timber being tested. A possible spacing in practice may be 150 mm, which caters for many types or species of wood. However, more benefit is provided by a closer spacing, say between 25 mm and 50 mm.

Similarly, measuring the clear stiffness of the timber length may comprise stressing the timber length at a plurality of positions spaced along its length while the timber length is supported so that each stressing is midway between the supports, determining the stiffness of the timber length at each position where it is stressed, and selecting each of a plurality of the values for stiffness so obtained for determining the clear stiffness of the timber length. Thus, for example, a proportion of the highest values obtained for stiffness may be selected, the average thereof being taken as the clear stiffness of the timber length. As will emerge hereunder the highest values need not necessarily be selected, but they are preferred, as providing the grading method of the invention with a built-in safety margin.

The spacing between the positions at which the timber length is stressed to measure its clear stiffness, may be the same as the spacing between the positions at which the timber length is stressed to measure its minimum stiffness. Conveniently the timber length is stressed at the same positions to determine both minimum stiffness and clear stiffness.

Usually, when the timber length is stressed, the two spaced supports across which it is supported will be at a fixed spacing from each other. This means that the end portions of the timber length, i.e. the portions which are closer to the ends of the timber length than half the span between the two spaced supports, cannot be loaded and stressed. Thus, in accordance with the method, the minimum stiffness of a central portion along the length of the timber length may be measured, being taken as the minimum stiffness of the whole timber length, the end portions of the timber length on opposite sides of the central portion each being half as long as the span between the supports. Similarly, the clear stiffness of said central portion may be measured, being taken as the clear stiffness of the length. The span between the supports may be for example, 600 mm.

Confining the measurements of minimum stiffness and clear stiffness to the central portion of the timber length is in no way a practical disadvantage. This is because, in practice, the span between the supports can be arranged to be relatively short in relation to the overall lengths of the timber lengths to be graded, so that the end portions are relatively short compared with the length of the central portion. Furthermore, when the timber lengths are eventually put to use as load supporting members in constructional work, they will usually be subjected to stresses such that they will be more heavily stressed towards their centres than near their ends. The existence of defects or zones of low stiffness at their ends is thus of little practical significance, in decreasing their usefulness, compared with the existence of defects towards their centres.

According to the method, for two timber lengths of the same clear stiffness, the timber length having the higher minimum stiffness may be classified into a higher grade than the timber length having the lower minimum stiffness.

By "higher grade" is meant a higher or greater load bearing ability, for example when loaded as a simple beam supported at or near its ends, by means of a load applied at or near its centre.

Although it is possible to grade timber lengths according to the single predictor constituted by their minimum stiffness, this method of grading is inherently inaccurate and requires large safety margins, resulting in substantial wastage of rejected or downgraded timber. This safety factor leads to substantial losses in that timber is often sold at a lower grade than that to which it is entitled. The present method on the other hand uses the further and independent predictor of clear stiffness.

In this regard, it will be appreciated that for two boards having the same clear stiffness, the board having the higher minimum stiffness will have the greater load-bearing ability. On the other hand, in contrast, for two boards having the same minimum stiffness, the board having the higher clear stiffness will not in fact have a higher load-bearing capacity, but will have a lower load-bearing capacity. The reason for this, is that when the boards are stresses as simple beams, the board with the higher clear stiffness, will be stressed in such a way that stress concentration takes place at the position of minimum stiffness leading to early rupture at low load values. On the other hand, if the clear stiffness is somewhat less, then the timber length as a whole will flex more than for a high clear stiffness, thereby sharing the stresses to which the board is subjected at the point or position of minimum stiffness, thereby reducing stress concentration at such minimum stiffness and dissipating the stress. Thus while the board with the lower clear stiffness will tend to flex more than the board with the higher clear stiffness, it will be able to accept a greater load before rupture. Thus the load bearing ability of a board does not depend merely on its minimum stiffness at any position along its length, but also on its clear stiffness, i.e. its stiffness along the remainder thereof, or, expressed differently, the load bearing ability of the board depends on the minimum stiffness and also on the difference between the minimum stiffness and the clear stiffness. Thus, while the one predictor is the minimum stiffness, the other predictor can either be the clear stiffness or the difference between the clear stiffness and the minimum stiffness, the clear stiffness or the difference between the clear stiffness and minimum stiffness in this regard merely amounting to alternative ways of expressing the same feature of the board.

Bearing in mind that the minimum stiffness on the one hand and the clear stiffness or the difference between the clear stiffness and the minimum stiffness on the other hand are used as independent predictors in accordance with the invention, any suitable formula which takes both independent predictors into account to grade timber lengths, i.e. one which grades the timber lengths into higher grades when they have higher minimum stiffnesses, and one which grades them into lower grades when they have higher clear stiffnesses or higher differences between their clear stiffnesses and minimum stiffnesses, will provide a more accurate and more valuable grading system than one which relies only on minimum stiffness. This will lead to a reduction in the safety margin necessary, leading to a reduction, which can be substantial, of unnecessarily rejected or downgraded timber.

A method which the applicant has found to be particularly effective is one in which timber lengths having similar grades according to the formula $$G = 1 - \frac{\text{clear modules of elasticity} \times B}{\text{minimum modules of elasticity}}$$

where
G = the arbitrary grade of the timber length in terms of the maximum load it can carry when loaded as a simple beam without rupturing; and
B = an experimentally determined constant for timber lengths of the particular species and having the particular dimensions being graded,
are classified into the same class. Modulus of elasticity varies directly with (although not necessarily in direction proportion with) stiffness, so that the higher the clear stiffness the higher the clear modulus of elasticity, and the higher the minimum stiffness, the higher the minimum modulus of elasticity. It will thus be appreciated that in accordance with the above formula, the higher the clear modulus of elasticity for a particular board, the lower will be its grade, and the higher the minimum modulus of elasticity for a particular board, the higher will be its grade. Many other possible formulae can be used however, each of which is an improvement over formulae which merely employ minimum stiffness (or minimum modulus of elasticity) by itself as a predictor.

In one convenient embodiment the method may comprise continuously moving the length of timber, stressing the moving length of timber by applying a transverse load thereto, the length being supported by two supports between which the load is applied and the load causing a deflection of the timber length measuring the load and/or the deflection, thereafter stressing the moving length differently by applying a different load to the timber length at the same position while supported in the same fashion to obtain a different deflection, measuring the different load and/or the different deflection, and relating the original load and original deflection to the different load and different deflection according to predetermined criteria, thereby to grade the timber length. In this regard it is to be noted that various methods exist to obtain the minimum and clear stiffnesses required for the method of the invention, and handling a continuously moving length is merely one which lends itself to mechanisation and speed in the mass handling of timber lengths.

It will be appreciated that using differences in loads and deflections provides an important advantage of eliminating the effects of bow on measurements, as differences, e.g. increments, in loads related to differences, e.g. increments, in deflections can be used to grade the timber length.

The method may include applying the original load and the different load from the same side of the timber length, so that the length is in each case deflected in the same direction. The timber length may be freely supported as a simple beam during each stressing thereof, the length being substantially unconstrained during the stressing except by the load and the two supports between which the load is applied. Thus, during stressing, the board is supported essentially only by two supports which are spaced lengthwise relative to the timber length and which are located on one side of the timber length, the load being applied to the opposite side of the timber length, at a position, lengthwise relative to the timber length, between said supports. The load is, as mentioned above, conveniently applied midway between the supports.

The original and different loads, i.e. the original and different stressings, will according to this embodiment be applied to the length of timber at a plurality of spaced positions spaced lengthwise along the timber length. This is conveniently effected by in each case advancing the timber length past the supports, and stressing it in turn at said plurality of positions as it is so advanced, thereby enabling the minimum stiffness of the timber length to be determined; and also the position lengthwise along said timber length where it is of minimum stiffness. This enables the positions of zones of weakness such as knots in said timber length to be identified. The spaced positions should thus be as close together as is reasonably practicable.

As mentioned above, the length is conveniently supported as a simple beam with the load being applied midway between the supports. This is so that the maximum deflection is obtained for a particular loading, or so that the minimum loading is obtained for a particular deflection, to obtain the maximum sensitivity of the stressing for the most accurate results. The effects of imperfections such as knots are magnified when the loading takes place directly on such imperfections. The spacing between the positions will, as mentioned above, thus be so small that no significant imperfection will escape being loaded more or less directly, so that it is identified and so that the reduced stiffness caused by the imperfection is properly measured.

As mentioned above, the applicant has found that, by relating the minimum stiffness of the timber length to the clear stiffness of the timber length, i.e. by using both the minimum stiffness and the independent predictor of clear stiffness in conjunction, improved prediction of the grade of the timber can be achieved, thereby leading to reduced unnecessary rejection of timber lengths. In other words, a lower margin of error is provided by the greater degree of accuracy of the method, and a lower proportion of timber lengths are assigned to grades which are lower than the actual grades to which they are entitled.

The effect of imperfections is magnified, and sensitivity of grading to imperfections and to determining their location is increased, if the span between the supports is kept as low as practicably possible. The use of the lowest practicable span between supports during loading to magnify the effect of imperfections on stiffness, requires increased sensitivity of measurement, as deflections caused by loading become smaller together with the reduction in span. It is thus preferred, in measuring the stiffness of the board, to measure the loads which cause fixed deflections, rather than the deflections caused by fixed loads.

Each original load may be applied at one location, the timber length then being moved to another location where each different load is applied. Thus, two pairs of supports may be provided at different locations provided by two different work stations, the timber length being stressed at one work station, and moved to the other work station, where the different stress is applied. Thus the method may comprise advancing the timber length past said locations, and stressing the timber length at the same positions along its length at each of the locations. At each work station or location where the timber length is stressed, the spacings between the positions along the length of the timber length where it is stressed are as mentioned above preferably the same, and the positions themselves are preferably the same, so that the positions where the different loads are applied to the timber length are the same positions as, and coincide with, the positions where the load was applied at the first location during the original stressing.

The timber length may thus be advanced continuously past said locations, and may be moved continuously from the first location to the second location. If the timber length is a board, it preferably has its major faces vertical, and is stressed normal to its major faces, the load being applied in a horizontal direction to one of the major faces of the board.

The method may include measuring the thickness of the timber length, and using said thickness in conjunction with the loadings and deflections, to grade the length, the thickness being used for example in determining the modulus of elasticity of the length.

The thickness of the board may be measured before the first stressing, and its actual thickness can be used, optionally, in conjunction with other factors such as timber species, the width of the board and the like, to determine a suitable original stressing to which the length is subjected. Instead, as mentioned above, the thickness measured need only be used to obtain the modulus of elasticity, and the nominal thickness of the board may be used to fix the original stressing.

In this regard "thickness" means the cross sectional dimension of the timber length transverse to the timber length, in the direction in which the load of the stressing is applied. "Width" is correspondingly the cross sectional dimension of the length, transverse to its lengthwise direction, normal to the direction in which thickness is measured. For a timber length in the form of a board which is loaded on one of its major faces, the width will thus be the dimension of the board transverse to its length, across its major faces, and the thickness will be the spacing between its major faces.

When the timber length is advanced past the supports, for example when it is advanced past the first and second locations at the work stations, the method may include measuring its thickness at a plurality of positions spaced along its length, thereby to obtain an indication of the average thickness of the timber length, for better prediction of stiffness and grading. The spacings between the positions at which thickness is measured conveniently are the same as the spacings between the positions where the board is stressed.

Conveniently, when determining the stiffness of the timber length at a particular position, the average thickness of the timber length at and on opposite sides of the position where it is loaded may be used to calculate its stiffness. The distance along the board over which this average thickness is taken into account for measuring stiffness at a particular position, may comprise, say, two or three load spacings on opposite sides of the position in question. Thus if the board is loaded every 50 mm along its length, its thickness averaged over a length of 200–300 mm may be used to calculate stiffness, the load being applied to the centre of the portion over which thickness is averaged.

The deflection obtained from each original stressing may be used to predict a suitable non-destructive load to which the length is to be subjected during the corresponding different stressing. Thus the method may comprise using the load applied to stress the length and the deflection obtained thereby during the original stressing, together with such factors as the thickness, cross section and type of timber of the timber length, to predict an increased different stressing to which the length can safely be subjected, said predicted increased stressing being applied during the subsequent different stressing. Thus the original stressing is preferably at low values of load and deflection, and the subsequent different stressing is then carried out at the highest non-destructive stressing which the timber length is predicted as being capable of withstanding, thereby to achieve the largest differences between the loads in the two stressings and the largest differences in deflections in the two stressings, for enhanced accuracy.

The method may be computer-controlled, so that all the method steps are automatically carried out in a predetermined sequence. Thus the advancement of the timber length past said locations may be monitored by photo-electric cells or similar detection devices, operative via the computer to control the measurement of thickness, to control the degree of stressing in terms of load applied and deflection obtained, and to control the physical movement of the timber lengths.

To permit measurement of load rather than deflection, as mentioned above, each timber length is preferably advanced at a constant deflection past each of said locations, variations in load being measured at said locations by load cells such as load transducers.

The method may comprise using the computer automatically to grade the timber lengths, in accordance with their predicted strengths arising from the stressings applied at the said locations, and the method may comprise marking said boards accordingly, and marking and identifying boards having imperfections, the locations of the imperfections being identified and boards capable profitably of being sawn where the imperfections are located towards the ends thereof, also being identified.

The method of the present invention is conveniently carried out on a timber stress grading machine which comprises means for continuously moving a length of timber, means for stressing the moving length of timber by applying a transverse load thereto, the length being supported by two supports between which the load is applied, to cause a deflection of the timber length, means for measuring said load and/or deflection, means for then stressing the moving length differently at the same position while supported in the same fashion to obtain a different deflection, means for measuring the different load and/or the different deflection, and means for relating the original load and original deflection to said different load and different deflection according to predetermined criteria.

The means for applying the original load and the different load to the timber length may thus be arranged to act on the same side of the timber length, so that the length is in each case deflected in the same direction. The supports in each case may act freely to support the length as a simple beam during stressing thereof, so that the length is substantially unconstrained during stressing except by the load and the two supports between which the load is applied.

The machine may be adapted to apply the original load and the different load to the length of timber at a plurality of spaced positions spaced lengthwise along the timber length.

The means for relating the original load(s) and deflection(s) to the different load(s) and deflection(s) to grade the timber length will act to determine the minimum stiffness and clear stiffness of the timber length and to relate them to each other in grading the timber length.

The means for originally stressing the timber length is conveniently at one location, the means for differently stressing the length being at a different location and the machine including means for moving the timber length from the one location to the different location. However, it will be appreciated that the means for the original and different stressings may be the same means, at a single location, the timber length being moved past said location and stressed twice in succession.

The machine may include means for measuring the thickness of the timber length, the means for relating the original load and deflection to the different load and deflection being adapted to use the thickness measurement(s) so obtained, in the grading of the timber length.

The means for stressing the timber length differently may be responsive to the load and deflection of the original stressing, being adapted to provide said different load with a magnitude which depends on said original load and deflection.

The means for moving the timber length from the one location to the other may be adapted to move said length continuously.

When the machine is adapted to stress the timber lengths at different locations, as described above, the locations will each be at work stations having the supports for the timber length and the means for applying a load to the timber length arranged in substantially identical fashion. Thus, as described above, the spacing between the supports and the position of the means for applying the load between the supports will be the same at each work station, and the work stations will preferably be adapted to apply the load in the same direction at each work station.

The means for moving the timber lengths may comprise pairs of laterally spaced rollers, the pairs being spaced in series along the path which the timber lengths follow through the machine, said rollers conveniently having upright axes and being provided in the work stations, on a feed table leading to the first i.e. original work station, on an interconnecting table interconnecting the work stations, and on an outfeed table leading from the second i.e. different work station. Thus, the supports against which the timber lengths are stressed may be support rollers, and the means for applying the transverse load between said support rollers may also comprise a roller. Said rollers may further include, at each work station, a drive roller which conveniently is one of the support rollers, and may comprise, opposite each said support roller, a biassing roller whereby the timber lengths are biassed against the drive roller, said biassing roller conveniently being a pressure roller biassed by a fluid such as pneumatic fluid, under pressure.

As each timber length moves through the machine it will conveniently be held in the same attitude, and the load will be applied to the timber length from the same side of the timber length in each work station so that the length is in each case deflected in the same direction. The support rollers will support the timber length preferably as a simple beam. The surface along which the timber length moves, i.e. on which it slides as it moves between the rollers, in each work station will have a negligible effect on the accuracy of the stressing. When the timber length moves continuously through the machine, it is possible to apply the load continuously along the timber length as it moves, and to measure the load and deflection at closely spaced time intervals, corresponding to closely spaced positions lengthwise along the timber length. In this way the minimum stiffness and clear stiffness of the timber length can easily be obtained.

The machine may include means, such as a plurality of photo-electric cells, spaced along the path followed by the timber length through the machine, to detect and monitor progress of timber lengths through the machine. The machine may further include, at the first work station, the means for measuring thickness, which may be a thickness sensor which may comprise a transducer, whereby the thicknesses of timber lengths passing through the machine are measured.

At each work station the means for measuring the load applied may be a load cell, such as a load transducer, for measuring the load applied to each timber length as it is stressed in said work station.

Each work station will also include means for displacing the means for applying the load to the timber length, and means for measuring said displacement and hence the deflection of the timber length.

The means for advancing the timber lengths at each work station may include an impulse generator, and the machine may include means for marking information on the timber lengths as they pass through the machine.

Finally, the machine may include a control unit, such as a computer and memory system, for controlling advancement and movement of the timber lengths, and for controlling the stressing of the timber lengths as they are advanced through the work stations, in relation to the deflection and load applied thereto. This computer and memory system will act as the means for relating the original load and the original deflection to the different load and different deflection, according to the predetermined criteria, in the grading of the timber length. For each timber length it can determine the stiffness at any position at which it is measured on the timber length, and can determine the minimum stiffness and position thereof, and the clear stiffness by averaging a certain percentage or proportion of the stiffness measured, being the highest stiffness measured. When the thickness is measured and is taken into account by the computer in relating the original load and deflection to the different load and deflection, for each position where stiffness is measured, the computer can use the average thickness of the timber length for a short distance on opposite sides of the position where stiffness strength is measured, as described above.

The computer and memory system will be connected to and responsive to the photo-electric cells, to monitor the progress of each timber length along its path through the machine, for controlling the stressing of the timber lengths and thickness measurement thereof, in response to said progress. The computer and memory system may also be connected to and responsive to the thickness sensor, for controlling the amount of stressing applied to the timber lengths at the first work station, in response to changes in thickness between timber lengths passing through the machine; and said computer and memory system may be connected to the impulse generator of the first work station for operating the thickness sensor and for controlling the load applying means, so that the thickness of each timber length is sensed and so that each timber length is loaded at regular intervals along its length as it passes through the first work station, conveniently at the same equally spaced intervals. Likewise, said system may be responsive to the impulse generator of the second work station, for controlling the associated load applying means, to load such timber length at the second work station at regular intervals along its length, preferably at the same positions as it was loaded in the first work station.

Finally, the computer and memory system may be connected to and responsive to the load cell and displacement sensor of the first work station, thereby to control the stressing applied to each timber length at the second work station, in response to the displacement and load applied to that timber length at the first work station; and the system may be connected to the displacement sensor and load cell of the second work station, for comparing the load and displacement at the second work station with the load and displacement applied to the same timber length at the first work station, and for performing the necessary steps according to the predetermined criteria to grade the timber length using clear stiffness and minimum stiffness according to the method of the present invention; and said system may be connected to an information marking mechanism thereby to provide for the marking or grading and similar information on each graded timber length.

The invention will now be described, by way of example, with reference to the accompanying diagrammatic drawing, in which the single FIGURE shows a plan view of a timber stress grading machine suitable for carrying out the method of the present invention.

In the drawing, reference numeral 10 generally designates a timber stress grading machine. The machine comprises an infeed table 12, a first work station generally designated 14, a second work station generally designated 16, an interconnecting table 18 connecting the station 14 with the station 16, and an outfeed table 20 from the station 16. The machine 10 is suitable for stress grading timber lengths in the form of sawn or planed wooden boards. The tables 12, 18 and 20 are horizontal, and are adapted to move boards along a predetermined path through the machine 10, by means of holding rollers 22. The rollers 22 (22.1 and 22.2 as described hereunder) are arranged in pairs spaced longitudinally along the tables, the rollers of each pair being spaced laterally, and straddling the path along which the boards move.

One of the rollers of each pair, marked 22.1, is a double roller and is driven, the other, marked 22.2, being an idler roller. The double roller 22.1 is mounted on a lever 23.1 pivotally mounted at 23.11 about an upwardly extending axis. The roller 22.2 in each case is mounted on a lever 23.2, likewise pivotally connected about an upwardly extending axis at 23.22. The levers 23.1, 23.2 are interconnected by a pneumatic piston and cylinder assembly 24, which is connected to the lever 23.1 at 24.1 about an upwardly extending pivotal axis, and to the lever 23.2 at 24.2 about an upwardly extending pivotal axis. Extension of the assembly 24 moves the rollers 22.1, 22.2 away from each other and contraction of said assembly moves said rollers together, thereby to grip a board therebetween. The holding rollers of the table 18 are drivingly connected to the drive of the first work station 14 (described hereunder) by a V-belt drive (not shown). The holding rollers 22 of the infeed table 12 and outfeed table 20 may be similarly connected to the drives respectively of the first work station 14 or the second work station 16, or may be otherwise suitably driven.

Each work station 14, 16 comprises a pair of support rollers, namely a drive roller 26 and an idler support roller 28, which are spaced by 500 mm from each other in the direction of the path followed by boards through the machine. Each support roller 26, 28 is provided, opposed thereto and on the opposite side of said path, with a pneumatically operated biasing or pressure roller 30 adapted to hold a board passing through the machine against the associated support roller 26, 28. Each work station is provided with load applying means in the form of an idler roller 32 mounted on a pneumatic displacement regulator 34 whereby it is transversely, i.e. laterally, displaceable, relative to the path taken by boards through the machine. The regulator 34 includes a hydraulic piston and cylinder assembly for damping its motion.

Said idler rollers 32 are each provided with a load transducer associated with their displacement regulators 34 for measuring the load applied by the roller 32 to a board spanning the associated rollers 26, 28.

A plurality of photo-electric cells, for sensing and monitoring the progress of boards through the machine, is provided in series along the machine. The photo-electric cells are designated (for the work stations 14, 16 and table 18) 36.1 to 36.12. Cell 36.1 is located immediately upstream of the support roller 26 of station 14 and downstream of the rollers 22 of the table 12, cell 36.2 being located upstream of the roller 32 and downstream of the roller 26 of the table 14.

Cells 36.3 to 36.10 are spaced in series from the upstream end of the table 18 to the downstream end thereof, each cell being located slightly upstream from an associated pair of rollers 22 on the table 18. Cells 36.11 and 36.12 are located in the station 16, at the same positions respectively as are occupied by the cells 36.1 and 36.2 in the station 14. Similar cells (not shown) can be provided on the tables 12 and 20, upstream of the pairs of rollers 22 thereon, in the same fashion as for the table 18, for the same purpose as described hereunder for table 18.

The station 14 is provided with a thickness sensor 38 comprising a transducer immediately upstream and associated with upstream roller 30, for sensing the thickness of boards travelling through the machine. The stations 14, 16 are also each provided with a displacement sensor 40 comprising a transducer, for sensing displacement of the roller 32 of the associated work station.

A marking mechanism is provided immediately downstream of the work station 16, in the form of a printing table, generally designated 42. On the printing table 42 are provided, spaced longitudinally along the path taken by a timber length through the machine, a drive roller 44.1 and, downstream thereof, an idler roller 44.2. Opposite the rollers 44.1 and 44.2 are pneumatically operated pressure rollers 44.11 and 44.21 respectively. Between the rollers 44.1 and 44.2 are a plurality of stampers 44.3 which act as marking mechanisms for marking the timber length grade, and other desired information on each timber length. They are operated by double-acting pneumatic piston and cylinder mechanisms 44.31. The table 42 is mounted so that is easily and lightly movable laterally relative to the path through the machine taken by the timber lengths, and so that its influence on the deflection of a timber length moving out from the second work station 16 and still being deflected by said second work station 16, is negligible and does not influence the accuracy of results obtained from the second work station 16.

The displacement sensors 40 are mounted to be movable with the associated rollers 32. The rollers 28 are provided with impulse generators 45, the function of which will be described hereunder.

The machine 10 also includes a computer and memory system, in the form of a unit, generally designated 46.

The work stations are respectively provided with hydraulic motors 47 which are connected to a hydraulic power source 47.1 located at the second work station 16, and the machine further includes various types of anciliary electrical and service equipment (not shown) including means for adjusting the gap between the rollers 26, 28 and their associated rollers 30 when boards are not between them; comparators; selectors; switches; display units; relays, pilot lights, analogue scales and the like.

The computer and the information storage unit 46 is operatively connected to the photo-electric cells on the tables 12 and 20 and to the cells 36.1 to 36.12, to the thickness sensor 38, to the load transducers at 34 associated with the rollers 32, and to the displacement sensors 40, to receive data therefrom, and to store such data temporarily, when necessary. The unit 46 is also operatively connected to the displacement regulators 34, and to the marking mechanisms on the table 42, to control operation thereof in response to data received by the unit 46. The unit 46 is also connected to the drive motors 47 and thence to the rollers 22 and 26, to control operation thereof in response to data received by the unit.

Typically, the machine 10 is suitable for grading rough sawn or preferably planed timber boards of a thickness in the range 20-55 mm, width in the range 75-315 mm, and length in the range 1200-7900 mm, the boards passing through the machine at a speed between 25 and 150 meters a minute. For boards of this nature, the suitable span between the support rollers 26 and 28 in the respective stations 14 and 16 is, as mentioned above, 500 mm. In use, the machine 10 is set up to grade boards of a particular nominal width and thickness, and timber of a particular species, and of a specified minimum length, the unit 46 being preprogrammed accordingly, and the drive motors 47 being set to move the boards through the installation at a desired appropriate grading speed. The programming will include predetermined stiffness limits for grades of timber; information regarding safe or non-destructive bending stresses to which boards of the type being tested can be subjected; the depth of indentation by the various rollers of the board surfaces anticipated, caused by pressure of the rollers on the timber; the moisture content of the timber; changes in span and neutral axis datum line of the timber caused by deflection thereof during loading, etc.

In use, boards to be graded are fed sequentially into the machine, supported on edge on the table 12, the leading end of each board being fed in turn between the rollers 22 on said table 12.

When the leading end of the board is sensed by the cells 36 associated with the pairs of rollers 22 on the table 12 these rollers are activated by the unit 46 so that the rollers 22 of each pair move towards each other, to grip the board between them. At the same time the rollers 22 are driven to move the board along the table 12 and to advance the board into the work station 14. To move the board and hold it, only the two pairs of rollers nearest the leading edge of the board need be activated at any one time, the pairs of rollers 22 upstream thereof being released in sequence as the board moves along.

When the leading end of the board is sensed by the cell 36.1 the impulse generator 45 on the roller 28 of the work station 14 is activated to generate pulses which enable the thickness sensor 38 and the load transducer associated with the associated roller 32 to take appropriate measurements at spaced positions along the length of the board as described hereunder. The photo-electric cell 36.1 also activates the displacement regulator 34 associated with the roller 32 of the work station 14, which regulator 34 starts moving the associated roller 32 across the path of the board towards the rollers 26 and 28.

Simultaneously the load transducer associated with the roller 32 in the work station 14 is activated, and it starts to transmit force values to the unit 46 as soon as the leading end of the board comes into contact with the roller 32.

When the leading end of the board operates the photo-electric cell 36.2, the thickness sensor 38 associated with the roller 30 transmits a measurement of the thickness of the board to the unit 46.

The unit 46, from the actual thickness of the board measured by the thickness sensor 38, can, if desired, determine from pre-programmed information as to the safe bending stress for the timber in question, a suitable deflection for stressing the board between the rollers 26 and 28 on the one hand, and 32 on the other hand. The unit simultaneously computes what force must be applied by the roller 32 to the board to locate the roller 32 at a displacement from its starting position which corresponds to this deflection.

The roller 32 at this stage is still being moved towards the rollers 26 and 28 by the displacement regulator 34, and the associated load transducer is continuing to transmit measurements of the force applied to the board to the unit 46, for comparison with said computed value. As soon as the force reaches this computed value, the displacement regulator 34 is stopped by the unit 46, thereby fixing the displacement of the roller 32 towards the rollers 26 and 28, at a value corresponding with the computed suitable deflection of that particular board as a beam between the rollers 26 and 28. It will be appreciated that at this stage, the board is still being held between the pairs of rollers 22 on the table 12, and between the roller 26 and its associated roller 30, and is being loaded cantilever fashion by the roller 32.

However, instead of using the actual thickness of the board to determine what deflection or load should be provided at the first work station 14, it may be more convenient merely to use the nominal thickness of the board to provide a predetermined and fixed deflection in the first work station.

Once the leading edge of the board reaches the roller 28, e.g. at a fixed time interval after it has passed the cell 36.2, the rollers 22 on the table 12 will be caused to release the board. The board will then be gripped between the rollers 26 and 28 on the one hand, and the rollers 30 and 32 on the other hand, and will be stressed as a simple beam over the 500 mm span provided by the rollers 26 and 28, by the roller 32. At this stage, the load transducer associated with the roller 32, in response to the impulse generator associated with the roller 28, starts transmitting force values at 50 mm intervals along the length of the board to the unit 46 for storage and use as described hereunder, the board passing through the work station 14 at a constant deflection determined by the displacement of the roller 32 towards the rollers 26 and 28.

At the same time, in response to the impulse generator 28 the thickness sensor 38 starts to transmit further thickness values to the unit 46. These thickness values are, likewise, transmitted at 50 mm intervals along the length of the board.

When the trailing end of the board reaches the photo-electric cell 36.1, the impulse generator associated with the roller 28 is deactivated, and transmission of thickness and force values by the thickness sensor 38 and the load transducer associated with the roller 32 to the unit 46 is discontinued. The displacement regulator 34 at the same time automatically retracts the roller 32 with its associated load transducer and displacement sensor to their starting position, and according to the preset minimum length of the boards being graded, the appropriate number, e.g. the first two holding rollers 22 on the table 18 are at the same time activated to move the board along the table 18 towards the work station 16. Detection by the photo-electric cell 36.1 of the trailing end of the board likewise releases via the unit 46 an interlock between said cell 36.1 and the table 12, thereby permitting the table 12 to operate again for the succeeding board.

As the board progresses along the table 18, the photo-electric cells 36.3 to 36.10 via the unit 46 activate suitable associated pairs of rollers 22, to keep said board in motion, while deactivating such pairs of rollers 22, upstream of the operative pairs, which are not required. The number of rollers simultaneously activated comprises the two pairs of rollers 22 closest to the leading end of the board. It will be appreciated that activating involves moving the rollers of each pair together to grip the board, while rotating the rollers to move the board, and deactivating the rollers correspondingly involves moving them apart and disconnecting them from the hydraulic drive 47 of the station 14. The V-belt drive of the rollers 22 of the table 18 is, as a safety feature, arranged such that boards cannot move along the table 18 more slowly than they move through the station 14.

While the board is moving along the table 18 the unit 46 computes the highest stiffness value obtained along the length of the board at the work station 14 from the constant deflection of said board and from the highest force reading transmitted by the load transducer. The unit then computes from this highest stiffness value and a pre-programmed safe maximum bending stress, the highest non-destructive stress which the board should be capable of withstanding in the work station 16, together with the displacement of the roller 32 of the station 16 required to produce this stress of the board.

When the leading end of the board reaches the photo-electric cell 36.11 the associated displacement regulator 34 starts moving the roller 32 towards the associated rollers 26 and 28 to achieve this computed displacement. When the leading end of the board reaches the roller 28, as with the station 14, the pulse generator of the associated drive roller 28 is activated. The associated displacement sensor 40 transmits said displacement to the unit 46 and the displacement regulator 34 is stopped when the computed displacement is reached.

When the leading end of the board reaches the roller 28, the remaining operative holding rollers 22 on the table 18 are released, the other holding rollers on the table 18 having previously been released.

The board will once again be loaded at substantially the same positions, spaced 50 mm apart, as it was loaded at in the work station 14, and in this regard it is to be noted that the spacing between the rollers 26, 28 in the station 16 is the same as in the station 14, and that the roller 32 is once again midway between the rollers 26 and 28. The geometry and arrangement of the rollers 26, 28 and 32 is thus the same at the two stations 14 and 16, although the station 16 and its rollers and other parts can be of heavier and more robust construction than those encountered in the station 14, to cater for the higher stresses encountered in the station 16.

When the leading end of the board reaches the roller 28 the load transducer associated with the roller 32 transmits the force values required to load the board to said constant deflection to the unit 46 in response to the pulses generated by the pulse generator associated with the roller 28, the board again being gripped, as in the station 14, between the rollers 26, 28 and the rollers 30, 32 and being loaded as a simple beam by the roller 32 with the rollers 26, 28 as supports.

When the trailing end of the board reaches the photoelectric cell 36.11 said pulse generator is deactivated and the displacement regulator 34 moves the roller 32 with the associated displacement sensor 40 to their starting positions, ready for the next board and the holding rollers 22 on the table 20 are activated to remove the board from the station 16.

It will be appreciated in this regard that while the board is leaving the station 16 and is entering the rollers on the table 20, it will be passing through the printing table 42 across which it is driven by the roller 44.1 in conjunction with the rollers 44.2, 44.11 and 44.21. Before the timber length has left the printing table, the unit 46 will have calculated the grade of the board and other data such as the grades of various sections of the board, the zones of weakness and the zone of greatest weakness of the board, and the like, and such data will be marked on the board.

The unit 46 will be pre-programmed according to statistically sufficient data obtained from boards of the same species or type of wood and of the same nominal dimensions, tested e.g. under laboratory conditions on a simple bending beam apparatus having its supports at the same spacing as rollers 26 and 28, and having a central loading mechanism at the same relative position as the roller 32. Thus predictable qualities of the wood such as stiffness, maximum safe value for non-destructive stressing of a particular species, average knot size, etc. can be determined beforehand. The unit 46 is programmed to take such measurements as are necessary to grade each board from the data supplied to it by the various sensors in the machine, when the board passes through the machine, and to relate them to one another according to the method of the invention. When each board has been graded, the data pertaining to it are discarded and its circuits are cleared to deal with the succeeding board.

If desired, the machine can be provided with one or more digital counters, to indicate the total number of boards graded, and the number of boards in each grade. Furthermore, the number of positions on each board corresponding to each different grade can be counted, if necessary.

According to the method of the present invention, as the board passes through the work station 16 a predetermined number of the highest values of modulus of elasticity (corresponding directly with and derived directly from the corresponding number of the highest values for stiffness) obtained from the data measured at the various positions 50 mm apart are averaged by the unit 46 to obtain the clear modulus of elasticity for the board. As mentioned above, using a preportion of the highest values is to a certain extent arbitrary, as the average value of stiffness or modulus of elasticity for the whole board could be used as the clear value, or an average or mean (weighted if desired) of predetermined intermediate values. Using the highest values (e.g. the five highest) to obtain the clear value however has a built-in safety factor as it will magnify the undesired effect of any stress concentration in the weakest part of the board when loaded, thus leading to a conservative grading. Similarly, the minimum modulus of elasticity for the board is measured and the board is graded according to criteria which take into account both the clear modulus of elasticity i.e. the clear stiffness of the board, and the minimum modulus of elasticity, i.e. the minimum stiffness of the board. If desired, the difference between the clear value and minimum value can be used together with the minimum value in the grading (the higher the difference), the lower being the grade of the board, and the lower the minimum modulus, the lower the grade); or the minimum value and clear value can be used together in a fashion which does not rely on the difference therebetween to obtain the grade, but which merely grades more highly with a higher minimum value and grades less highly with a higher clear value.

As mentioned above, results obtained from stressing at the first work station are used to determine the highest safe non-destructive stressing to which the board can be subjected in the second station. The modulus of elasticity, i.e. the stiffness of the board, is obtained by known methods from a comparison between the increase in deflection obtained in the second station when compared with the first station, with the increase in load in the second station compared with the first station. This is done for each of the positions at 50 mm spacings along the board for which measurements are taken. In determining the modulus of elasticity, the actual thickness of the board at the exact position where strength is measured is not used by itself, but instead the average value of thickness of the board is used for short distances on either side of said position. Thus the average value of the measured thickness for the, say, five or seven positions straddling the position where load and deflection are measured, can be used for the thickness value, so as to increase accuracy and avoid the effects of local discrepancies in thickness.

Thus the modulus of elasticity is obtained for the board at each of a plurality of positions spaced 50 mm apart along the length of the board, except for those portions of the board at its ends which are too close to said ends to be able to be stressed across the support rollers 26, 28, i.e. those which are closer to the ends of the board than half the span between said rollers 26, 28.

From these values, the clear modulus of elasticity and the minimum modulus of elasticity for the portion of the board where measurements have been taken, can be obtained, as mentioned above.

The applicant has found that grading of boards according to the formula:

$$G = 1 - \frac{\text{(clear modulus of elasticity)} \times B}{\text{(minimum modulus of elasticity)}}$$

where
G = grade of timber
B = experimentally determined constant
gives substantially more accurate grading than prior systems known to the applicant. The improved grading is better in that, because it takes into account both the clear value and the minimum value for each board, it is of greater accuracy. Thus substantially fewer boards have to be rejected or assigned to grades which are lower than the actual grade to which they are entitled. The applicant has found that, by using the method of the invention incorporating the use of the above formula, the reduction in the number of boards which are incorrectly graded too low is such as to increase the total value of the boards graded by up to 20%.

In this regard it should however be noted that no particular significance is attached to the particular formula defined above, in that a number of different formulae are possible, each of which takes into account the clear stiffness of the board and the minimum stiffness of the board or, optionally, the difference between the clear stiffness and minimum stiffness. All of these formulae provide distinctly improved grading over methods which use only the minimum stiffness or modulus of elasticity and which neglect the clear stiffness or modulus of elasticity. The above defined formula is however one of the best and most easily applied in the applicant's practical experience with the machine described herein.

The method thus relates the clear and minimum stiffnesses by using the minimum stiffness or minimum modulus of elasticity, together with the independently measured clear stiffness or clear modulus of elasticity, to grade the board, the grade being dependent on both said minimum value and the clear value (or the difference between the minimum value and the independently measured clear value). The values measured can then be related as indicated above, for example by using the minimum stiffness or minimum modulus of elasticity, together with the independently measured clear stiffness or clear modulus of elasticity, to grade the board, the grade being dependent on both said minimum value and said clear value or the difference between them.

As the method is more accurate than those previously known to the applicant, a significant saving in incorrectly rejected or incorrectly downgraded timber can be achieved, as the margin of safety required in the grading is reduced. It is the employment of closely spaced measurements (about 50 mm) and reduced spans (about 500 mm) which permit the method to be applied with accuracy. The close spacings in measurements and reduced span give an accurate value for minimum stiffness, and magnify the effect of defects, while measurement of load changes at constant deflections permit accurate measurement at the reduced span employed.

Although the method of the invention has been described with reference to a relatively sophisticated automated apparatus, it will however be appreciated that the invention contemplates also use of simpler apparatus, provided it is capable of performing the steps required by the method. Thus, for example, the pairs of rollers 22.1, 22.2 may be omitted from the infeed and outfeed tables and any other suitable arrangement may be used for infeed and outfeed purposes.

I claim:

1. A method of stress-grading a timber length in terms of its load-bearing ability when loaded as a simple beam, which comprises
   measuring the minimum stiffness of the timber length;
   measuring the clear stiffness of the timber length; and
   using the independent predictors constituted by said minimum stiffness and said clear stiffness in conjunction to classify the timber length into a particular grade according to its load-bearing ability when loaded as a simple beam.

2. A method as claimed in claim 1, in which measuring the clear and minimum stiffness of the timber length comprises stressing the timber length at a plurality of positions along its length while it is supported as a beam, each stressing comprising loading the length transversely between two spaced supports supporting the length, and the load and the deflection caused by the load being related to determine the stiffness.

3. A method as claimed in claim 2, in which measuring the minimum stiffness of the timber length comprises stressing the timber length at a plurality of closely spaced positions along its length while the timber is supported so that each stressing is midway between the supports, determining the stiffness of the timber length at each position where it is stressed, and selecting the minimum value for stiffness so obtained as the minimum stiffness of the timber length.

4. A method as claimed in claim 3, in which the closely spaced positions are spaced apart by spacings which are of the order of the size of the knots anticipated to be encountered in the type or species of timber being tested.

5. A method as claimed in claim 3, in which the closely spaced positions are spaced apart by up to about 150 mm.

6. A method as claimed in claim 5, in which the closely spaced positions are spaced apart by a spacing between 25 mm and 50 mm.

7. A method as claimed in claim 3, in which measuring the clear stiffness of the timber length comprises stressing the timber length at a plurality of positions spaced along its length while the timber length is supported so that each stressing is midway between the supports, determining the stiffness of the timber length at each position where it is stressed, and selecting a plurality of the values for stiffness so obtained for determining the clear stiffness of the timber length.

8. A method as claimed in claim 7, in which a proportion of the highest values obtained for stiffness is selected, the average thereof being taken as the clear stiffness of the timber length.

9. A method as claimed in claim 7, in which the spacing between the positions at which the timber length is stressed to measure its clear stiffness, is the same as the spacing between the positions at which the timber length is stressed to measure its minimum stiffness.

10. A method as claimed in claim 9, in which the timber length is stressed at the same positions to determine both minimum stiffness and clear stiffness.

11. A method as claimed in claim 2, in which the minimum stiffness of a central portion along the length of the timber length is measured and is taken as the minimum stiffness of the timber length, the end portions of the length on opposite sides of the central portion each being half as long as the span between the supports.

12. A method as claimed in claim 11, in which the clear stiffness of said central portion is measured and is taken as the clear stiffness of the length.

13. A method as claimed in claim 1, in which for two timber lengths of the same clear stiffness, the timber length having the higher minimum stiffness is classified into a higher grade, than the timber length having the lower minimum stiffness.

14. A method as claimed in claim 13, in which for two timber lengths of the same minimum stiffness, the timber length having the lower clear stiffness is classified into a higher grade, than the timber length having the higher clear stiffness.

15. A method as claimed in claim 14 in which timber lengths having similar grades according to the formula:

$$G = 1 - \frac{\text{clear modulus of elasticity} \times B}{\text{minimum modulus of elasticity}}$$

where:
   G = the arbitrary grade of the timber length in terms of the maximum load it can carry when loaded as a simple beam without rupturing; and
   B = an experimentally determined constant for timber lengths of the particular species and having the particular dimensions being graded,
are classified into the same class.

* * * * *